United States Patent [19]

Priester et al.

[11] Patent Number: 4,490,390

[45] Date of Patent: Dec. 25, 1984

[54] SYNERGISTIC COMPOSITIONS OF CARBAMATE INSECTICIDES

[75] Inventors: Thomas M. Priester; Dennis R. Rayner, both of Wilmington, Del.

[73] Assignee: E. I. Du Pont de Nemours and Company, Wilmington, Del.

[21] Appl. No.: 399,968

[22] Filed: Jul. 19, 1982

[51] Int. Cl.$^3$ .................... A01N 33/24; A01N 37/00; A01N 41/06; A01N 43/08

[52] U.S. Cl. .................................. 424/298; 424/285; 424/300; 424/321; 424/327

[58] Field of Search ................ 424/298, 300, 327, 321

[56] References Cited

U.S. PATENT DOCUMENTS 3,576,834  4/1971  Buchanan .......................... 260/453
3,629,332 12/1971  Harrington et al. ................ 260/556
3,958,977  5/1976  Prochaska et al. .................. 71/103

FOREIGN PATENT DOCUMENTS 4727931  7/1972  Japan .................................. 424/321

Primary Examiner—Allen J. Robinson

[57] ABSTRACT

Carbamate insecticides are potentiated in their control of insects and mites when used in a composition with trifluoromethanesulfonamides.

2 Claims, No Drawings

SYNERGISTIC COMPOSITIONS OF CARBAMATE INSECTICIDES

BACKGROUND OF THE INVENTION

This invention relates to compositions of a carbamate insecticide and a trifluoromethanesulfonamide synergist for the insecticide.

Carbamate compounds are well known for their effective control of insects and mites that are destructive to agricultural crops. Carbamates, as are most insecticides, are usually more effective against some species of insects or mites than against others. Additionally, some species of insects or mites may develop strains that are resistant to the insecticides that had previously given effective control of the species. For reasons such as this, it is desirable to combine the insecticides with other compounds, known as synergists or potentiators, that can increase the activity of the insecticide against a broader range of insects or mites, against species that may have become resistant to the insecticide itself, or against species that are already susceptible to the insecticide.

SUMMARY OF THE INVENTION

The present invention provides insecticidal and miticidal compositions of:
(1) a carbamate insecticide; and
(2) a sulfonamide potentiator for the insecticide having the general formula

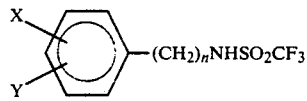

where X and Y, independently, are H, $CH_3$, F, Cl, Br, $OCH_3$, or $OCH_2CH_3$; or X and Y together are $OCH_2O$, $OC(CH_3)_2O$, or $CH_2CH_2CH_2$; and $n = 1-6$,
where the weight ratio of sulfonamide potentiator to insecticide is from about 1:5 to 10:1.

DETAILED DESCRIPTION OF THE INVENTION

The present invention is an insecticidal and miticidal composition of a carbamate insecticide and a trifluoromethanesulfonamide potentiator (or synergist) of formula I

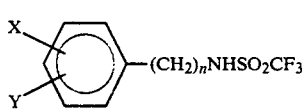

I where X and Y, independently, are H, $CH_3$, F, Cl, Br, $OCH_3$, or $OCH_2CH_3$, or X and Y together are $OCH_2O$, $OC(CH_3)_2O$, or $CH_2CH_2CH_2$; and n is an integer of 1–6.

It has been found that compounds of formula I, when used in a composition with carbamate insecticides, can potentiate the insecticide in a number of ways. They can increase the activity of the insecticide against species that may have developed a genetic resistance to the insecticide itself. They can increase the activity of the insecticide against species of insects or mites that are already susceptible to it, thereby reducing the quantity of insecticide necessary for effective control. In some situations, they can make the insecticide active against species over which it had previously produced little or no control, thereby broadening the spectrum of activity of the insecticide and making it a more effective agricultural tool. The sulfonamide compounds of this invention are found to be only slightly toxic to insects and mites themselves, but when used in conjunction with a carbamate insecticide, are found to potentiate the insecticide to result in mortality rates that exceed what would be expected from a purely additive effect of the carbamate insecticide and the sulfonamide compound used individually.

For example, one order of insects over which the potentiating effect of formula I compounds is quite evident is Lepidoptera. Within this order, the Family Noctuidae is well controlled, and the genus Heliothis within it, and particularly the species virescens (Tobacco budworm) within this genus, are especially well-controlled. It is to be understood, however, that the beneficial effects of the present invention are not limited to control of the Lepidoptera order or to any of the above-mentioned sub-classifications within it.

With respect to the sulfonamides of formula I, compounds that are preferred are those wherein X is individually H, F, Cl, or Br, Y is individually H; or X and Y together are $OCH_2O$; and $n=1-3$. Specifically preferred for their excellent potentiating activity and/or ease of synthesis are:
1,1,1-trifluoro-N-(3-phenylpropyl)methanesulfonamide
N-[2-(4-chlorophenyl)ethyl]-1,1,1-trifluoromethanesulfonamide
N-[2-(4-bromophenyl)ethyl]-1,1,1-trifluoromethanesulfonamide The compounds of formula I can be prepared as described in U.S. Pat. No. 3,629,332, herein incorporated by reference.

The carbamate insecticides that are beneficially potentiated in compositions with a compound of formula I are preferably methomyl, N-methylolmethomyl, oxamyl, carbaryl, thiodicarb (bis-methomyl), or carbofuran. Mixtures of two or more of these insecticides can also be used in the compositions.

Methomyl, the most preferred of the insecticides, is the common name for the methyl ester of N-(N-methylaminocarbonyloxy)ethanimidothioic acid and has the structure

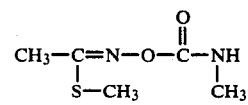

Methomyl can be prepared as described in U.S. Pat. Nos. 3,574,736; 3,576,834; and 3,787,470.

N-Methylolmethyl is the common name for the methyl ester of N-(N-hydroxymethyl-N-methylaminocarbonyloxy)ethanimidothioic acid and has the structure

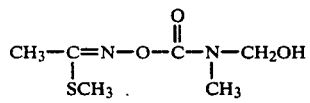

N-Methylolmethoxy can be prepared as described in U.S. Pat. No. 4,198,427.

Oxamyl is the common name for methyl N',N'-dimethyl-N-(methylcarbamoyloxy)-1-thioxamimidate and has the structure

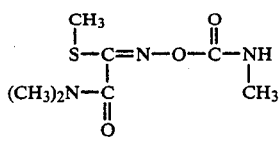

Oxamyl can be prepared as described in U.S. Pat. No. 3,530,220.

Carbaryl is the common name for 1-naphthyl N-methylcarbamate and has the structure

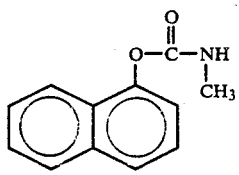

Carbaryl can be prepared as described in U.S. Pat. No. 2,903,478.

Thiodicarb is the common name for dimethyl N,N'-[thiobis-(N-methylimino-carbonyloxy)]ethanimidothioate and has the structure

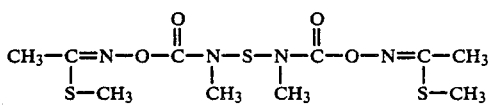

Thiodicarb can be prepared as described in U.S. Pat. No. 4,004,031.

Carbofuran is the common name for 2,3-dihydro-2,2-dimethyl-7-benzofuranyl methyl carbamate and has the structure

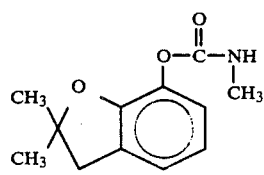

Carbofuran can be prepared as described in U.S. Pat. Nos. 3,474,170 and 3,474,171.

Insects and mites are controlled and agricultural crops protected by the composition of this invention by applying an effective amount of the composition (carbamate insecticide plus potentiator) to the locus of infestation or the area to be protected or directly on the insects or mites to be controlled. Direct application to the insects or mites is preferred since better results can be obtained thereby. The relative amount of potentiator used in the combination with the carbamate insecticide will depend on such factors as the identity of the insecticide, the species of insect or mite to be controlled, the pest's life stage, its size, its location, the time of year of the application, ambient moisture and temperature conditions, method of application, etc. In general, however, the potentiator is combined with the carbamate insecticide in a potentiator:insecticide weight ratio of about 1:5 to 10:1, preferably about 1:2 to 10:1.

The compositions of this invention will generally be used in formulation with a liquid diluent such as water or an organic solvent. Examples of such organic solvents are xylene and other aromatic solvents, acetone, isophorone, methyl isobutyl ketone, and other low molecular weight ketones. Applications can be made by spraying, for example, with either concentrated or dilute formulations of the active ingredients (potentiator plus insecticide) in the diluent. The formulations can be in the form of suspensions, solutions, or emulsions. Low volume applications, containing 10–80% by weight of the active ingredients, or high volume applications, containing 1% by weight or less of the active ingredients can be made. Application rates are more fully discussed below.

In addition to suspensions, solutions, and emulsions, other formulations of the present composition can be made with solid diluents as well. Such formulations include dusts, granules, wettable powders, emulsifiable concentrates, and the like. In general, the formulations contain about 0.1–99% by weight of active ingredients, and either or both of (a) about 0.1–20% by weight of a surfactant or (b) about 0.1–99% by weight of a solid or liquid diluent. More specifically, they will contain these ingredients in the approximate proportions set forth in Table I.

TABLE 1

| | Weight Percent* | | |
|---|---|---|---|
| | Active** Ingredients(s) | Diluent(s) | Surfactant(s) |
| Wettable Powders | 20–60 | 0–74 | 1–10 |
| Oil Suspensions, Solutions, Emulsions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules | 0.1–80 | 5–99.9 | 0–15 |

*Active Ingredient plus at least one of a Surfactant or a Diluent equals 100 weight percent.
**Carbamate insecticide plus a compound of formula I.

Lower or higher levels of active ingredient can be present, depending on the intended use and the physical properties of the compounds. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually grinding, as in a hammer or fluid energy mill. Suspensions are prepared by wet milling (see, for example, Littler, U.S. Pat. No. 3,060,084). Granules and pellets can be made by spraying the active material on preformed granular carriers or by agglomeration techniques. See J. E. Browning, "Agglomeration", Chemical Engineering, Dec. 4, 1967, pp. 147ff. and "Perry's Chemical Engineer's Handbook", 4th Ed., McGraw-Hill, New York, 1963, pp. 8-59ff.

Many of the formulations described above can be applied directly. Sprayable formulations, for example, can be extended in suitable media and can be used at spray volumes of from one to several hundred liters per hectare. With respect to the aforementioned formulations in general, insecticidally effective rates of about 0.05 to 34 kilograms of active ingredient per hectare are used. It is preferred to use rates of about 0.1 to 17, most preferably about 0.2 to 8, kilograms of active ingredient per hectare. Those skilled in the art will recognize, however, that application rates will depend on many of the factors mentioned earlier as affecting the relative weights of potentiator and insecticide.

The compositions of this invention can also be formulated with other agriculture-protecting compounds such as fungicides, bactericides, nematicides, acaricides, other insecticides, or other synergists. Total amounts of these other agriculture-protecting compounds can vary from 0.002–1 part by weight of the compounds per part of the composition (carbamate insecticide and potentiator). Suitable compounds of these kinds are well known. Examples are:

Fungicides:

methyl 2-benzimidazolecarbamate
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
N-(trichloromethylthio)tetrahydrophthalimide (captan)
N-(trichloromethylthio)phthalimide (folpet)
1-(4-chlorophenoxy)-3,3-dimethyl-1-(1H-1,2,4-triazol-1-yl)-2-butanone (triadimefon)
1-(4-phenylphenoxy)-3,3-dimethyl-1-(1H-1,2,4-triazol-1-yl)-2-butanol (bitertanol)
1-[2-(2,4-dichlorophenyl)-4-propyl-1,3-dioxolan-2-ylmethyl]-1H-1,2,4-triazole (propaconazole)
1-[2-(2,4-dichlorophenyl)-4-ethyl-1,3-dioxolan-2-ylmethyl]-1H-1,2,4-triazole (etaconazole)

Bactericides:

tribasic copper sulfate
streptomycin sulfate

Acaricides:

senecioic acid, ester with 2-sec-butyl-4,6-dinitrophenol ("Morocide")
6-methyl-1,3-dithiolo[4,5-b]quinoxalin-2-one ("Morestan")
ethyl 4,4'-dichlorobenzilate ("Folbex")
1,1-bis(p-chlorophenyl)-2,2,2-trichloroethanol ("Kelthane")
bis(pentachloro-2,4-cyclopentadien-1-yl) ("Pentac")
tricyclohexyl tin hydroxide ("Plictran")

Nematicides:

S-methyl 1-carbamoyl-N-(methylcarbamoyloxy)thioformimidate N-isopropylphosphoramidic acid, O-ethyl O'-[4-(methylthio)-m-tolyl]diester ("Nemacur")

Insecticides:

O-[2,4,5-trichloro-α-(chloromethyl)benzyl]phosphoric acid, O',O'-dimethyl ester ("Gardona")
2-mercaptosuccinic acid, diethyl ester, S-ester with thionophosphoric acid, dimethyl ester ("Malathion")
phosphorothioic acid, O,O-dimethyl, O-p-nitrophenyl ester (methyl parathion)
N'-(4-chloro-o-tolyl)-N,N-dimethylformamidine ("Galecron")
O,O-diethyl-O-(2-isopropyl-4-methyl-6-pyrimidylphosphorothioate ("Diazinon")
cypermethrin
permethrin
fenvalerate
tralomethrin
fluvalinate
deltamethrin
acephate

Synergists piperonyl butoxide
sesamex
sulfoxide

Formulation Examples

EXAMPLE A

| Oil Suspension | |
|---|---|
| 1,1,1-trifluoro-N—(3-phenylpropyl)methanesulfonamide | 10% |
| methomyl | 15% |
| polyoxyethylene sorbitol hexaoleate | 5% |
| highly aliphatic hydrocarbon oil | 70% |

The ingredients are ground together in a sand mill until the solid particles of methomyl are reduced in size to under about 5 microns. The methanesulfonamide stays dissolved in the hydrocarbon oil. The resulting suspension can be applied directly, but preferably not until after being extended with oils or emulsified in water.

EXAMPLE B

| Aqueous Suspension | |
|---|---|
| 1,1,1-trifluoro-N—(3-phenylpropyl)methanesulfonamide | 25% |
| methomyl | 10% |
| hydrated attapulgite | 3% |
| crude calcium ligninsulfonate | 10% |
| sodium dihydrogen phosphate | 0.5% |
| water | 51.5% |

The ingredients are ground together in a ball or roller mill until the solid particles of the methanesulfonamide and the attapulgite are reduced to diameters under 10 microns. The methomyl stays dissolved in the aqueous phase.

EXAMPLE C

| Solution | |
|---|---|
| 1,1,1-trifluoro-N—(3-phenylpropyl)methane-sulfonamide | 20% |
| methomyl | 20% |
| dimethylformamide | 60% |

The ingredients are combined and stirred to produce a solution which can be used for low volume applications.

EXAMPLE D

| Granule | |
|---|---|
| 1,1,1-trifluoro-N—(3-phenylpropyl)methane-sulfonamide | 2% |
| methomyl | 2% |
| dimethylformamide | 8% |
| granular attapulgite with particles ranging from 0.25 mm to 0.6 mm | 88% |

The methomyl and the trifluoromethanesulfonamide are first dissolved in the dimethylformamide and are then sprayed onto the attapulgite while it is being tumbled. Due to its low volatility, the solvent remains in the granule for an extended time but does slowly evaporate.

The other compounds of formula I can be formulated as granules in the same manner.

EXAMPLE E

| Wettable Powder | |
|---|---|
| N—[2-(4-bromophenyl)ethyl]-1,1,1-trifluoromethane-sulfonamide | 15% |
| methomyl | 35% |
| sodium alkylnaphthalenesulfonate | 2% |
| low viscosity methyl cellulose | 2% |
| diatomaceous earth | 46% |

The trifluoromethanesulfonamide is dissolved in methylene chloride which is subsequently sprayed onto diatomaceous earth. The treated diatomaceous earth is then blended with the methomyl and the other formulation ingredients listed above. The blend is then coarsely hammer-milled and air-milled to produce particles of powder essentially all below 10 microns in diameter. The product is reblended before packaging.

The other compounds of formula I can be formulated as wettable powders in the same manner.

EXAMPLE F

| Dust | |
|---|---|
| N—[2-(4-chlorophenyl)ethyl]-1,1,1-trifluoromethane-sulfonamide | 2% |
| methomyl | 2% |
| methylene chloride | 8% |
| granular attapulgite with particles ranging from 0.110 mm to 0.131 mm | 88% |

The methomyl and the trifluoromethanesulfonamide are first dissolved in methylene chloride and are then sprayed onto the attapulgite while it is being tumbled. Due to its high volatility, the solvent evaporates rapidly during the spraying operation.

The other compounds of formula I can be formulated as granules in the same manner.

EXAMPLE G

| Emulsifiable Concentrate | |
|---|---|
| 1,1,1-trifluoro-N—(3-phenylpropyl)methane-sulfonamide | 15% |
| methomyl | 15% |
| blend of oil soluble sulfonates and polyoxyethylene ethers | 4% |
| cyclohexanone | 66% |

The ingredients are combined and stirred gently until a homogeneous solution is achieved. A fine screen filter is used in packaging operation to insure the absence of any extraneous undissolved material in the product.

UTILITY EXAMPLES

EXAMPLE 1

Potentiation of Methomyl by Trifluoromethylsulfonamides

Mixtures of methomyl and sulfonamide synergists (1:1 weight ratio) and methomyl alone were dissolved in acetone. In a series of tests, several different doses of each mixture were topically applied to methomyl-resistant *Heliothis virescens*, 3rd instars, via the application of 1-microliter amounts of solution to the prothorax of the insects. After treatment, the insects were allowed to remain in isolation chambers (1 oz. cup, filled to 25% capacity with Bioserv ® synthetic diet) for 48 hours, after which time the insects were scored for mortality. For each test of each dosage, the $LD_{50}$ and $LD_{95}$ (does which kills 50 and 95% respectively of the treated insects) were calculated by a Bliss-Finney log dose-probit analysis. Since the sulfonamides used alone were found to have no observable effect at the highest concentration tested, these concentrations were ignored for the purpose of calculating the LD values. A synergism indicator was calculated using these data as follows:

$$SR_{95} = \frac{LD_{95} \text{ methomyl alone}}{LD_{95} \text{ methomyl when combined with potentiator}}$$

where $SR_{95}$ is the synergism ratio at the $LD_{95}$ level. The synergism indicator at the $LD_{50}$ level, $SR_{50}$, is calculated similarly.

All mixtures reported below, when applied against methomyl-resistant *Heliothis virescens*, 3rd instars, generated SR values greater than unity, indicating synergism.

TABLE 1A

Methomyl alone against methomyl-resistant *Heliothis virescens* 3rd instars (48 hour topical mortality).

| Dosage*** µg/insect | Mortality Tests | | | | | | | Kill % |
|---|---|---|---|---|---|---|---|---|
| | A X/10* | B X/10 | C X/10 | D X/10 | E X/10 | F X/10 | Total** | |
| 1.3 | 0 | | | 0 | | | 0/20 | 0 |
| 2.5 | | 2 | 1 | 0 | 0 | 0 | 3/50 | 6 |
| 5. | 1 | 3 | 3 | 1 | 2 | | 10/50 | 20 |
| 10. | | 2 | 2 | 1 | 0 | 3 | 8/50 | 16 |
| 25. | 4 | 2 | 5 | 3 | 3 | | 17/50 | 34 |
| 50. | | 7 | 4 | 3 | 4 | 3 | 21/50 | 42 |
| 100. | 7 | 7 | 4 | 3 | 3 | | 24/50 | 48 |
| 200. | 5 | 5 | 7 | 6 | 5 | | 28/50 | 56 |
| 400. | 7 | 10 | 8 | 5 | 7 | | 37/50 | 74 |

TABLE 1A-continued

Methomyl alone against methomyl-resistant *Heliothis virescens* 3rd instars (48 hour topical mortality).

| Dosage*** μg/insect | Mortality Tests | | | | | | | |
|---|---|---|---|---|---|---|---|---|
| | A X/10* | B X/10 | C X/10 | D X/10 | E X/10 | F X/10 | Total** | Kill % |
| Control | 0 | 0 | 0 | 0 | 0 | | 0/50 | 0 |

$LD_{50} = 96$
$LD_{95} = 8300$

\* Number of insects killed in the test (X) / Number of insects treated in the test
\*\* Total Number of insects killed in all tests (ΣX) / Total Number of insects treated in all tests
\*\*\*active ingredient(s) only

TABLE 1B

Methomyl plus N—[(2-(4-bromophenyl)ethyl)]-1,1,1-trifluoromethanesulfonamide (potentiator) (1:1 weight ratio) against methomyl-resistant *Heliothis virescens* 3rd instars (48 hour topical mortality).

| Mixture | | Mortality Tests | | | |
|---|---|---|---|---|---|
| Methomyl μg/insect | Potentiator μg/insect | A X/15 | B X/30 | Total | Kill % |
| 2.5 | 2.5 | 4 | 10 | 14/45 | 31 |
| 5. | 5. | 6 | 9 | 15/45 | 33 |
| 10. | 10. | 7 | 13 | 20/45 | 44 |
| 20. | 20. | | 18 | 18/30 | 60 |
| Control | | 0 | 0 | 0/45 | 0 |

$LD_{50} = 13.$  $SR_{50} = 7.4$
$LD_{95} = 1400.$  $SR_{95} = 5.9$

N-[(2-(4-bromophenyl)ethyl)]-1,1,1-trifluoromethanesulfonamide alone gives no mortality at 20 μg/insect.

TABLE 1C

Methomyl plus 1,1,1-trifluoro-N—(4-phenylbutyl)methanesulfonamide (potentiator) (1:1 weight ratio) against methomyl-resistant *Heliothis virescens* 3rd instars (48 hour topical mortality).

| Mixture | | Mortality Tests | | | |
|---|---|---|---|---|---|
| Methomyl μg/insect | Potentiator μg/insect | A X/15 | B X/30 | Total | Kill % |
| 2.5 | 2.5 | 4 | 17 | 21/45 | 47 |
| 5. | 5. | 2 | 19 | 21/45 | 47 |
| 10. | 10. | 7 | 21 | 28/45 | 62 |
| 20. | 20. | | 28 | 28/30 | 93 |
| Control | | 0 | 0 | 0/45 | 0 |

$LD_{50} = 4.1$  $SR_{50} = 23.$
$LD_{95} = 67.$  $SR_{95} = 120.$ 1,1,1-trifluoro-N-(4-phenylbutyl)methanesulfonamide alone gives no mortality at 20 μg/insect.

TABLE 1D

Methomyl plus 1,1,1-trifluoro-N—(2-phenylethyl)methanesulfonamide (potentiator) (1:1 weight ratio) against methomyl-resistant *Heliothis virescens* 3rd instars (48 hour topical mortality).

| Mixture | | Mortality Tests | | | | |
|---|---|---|---|---|---|---|
| Methomyl μg/insect | Potentiator μg/insect | A X/15 | B X/30 | C X/30 | Total | Kill % |
| 2.5 | 2.5 | 2 | 13 | 11 | 26/75 | 32 |
| 5. | 5. | 4 | 15 | 20 | 39/75 | 52 |
| 10. | 10. | 5 | 14 | 16 | 35/75 | 47 |
| 20. | 20. | | 21 | 19 | 40/60 | 67 |
| Control | | 0 | 0 | 0 | 0/75 | 0 |

$LD_{50} = 7.2$  $SR_{50} = 13.$

TABLE 1D-continued

Methomyl plus 1,1,1-trifluoro-N—(2-phenylethyl)methanesulfonamide (potentiator) (1:1 weight ratio) against methomyl-resistant *Heliothis virescens* 3rd instars (48 hour topical mortality).

| Mixture | | Mortality Tests | | | | |
|---|---|---|---|---|---|---|
| Methomyl μg/insect | Potentiator μg/insect | A X/15 | B X/30 | C X/30 | Total | Kill % |
| $LD_{95} = 1100.$ | | | | $SR_{95} = 7.5$ | | |

1,1,1-trifluoro-N-(2-phenylethyl)methanesulfonamide alone gives no mortality at 20 μg/insect.

TABLE 1E

Methomyl plus 1,1,1-trifluror-N—(3-phenylpropyl)methanesulfonamide (potentiator) (1:1 weight ratio) against methomyl-resistant *Heliothis virescens* 3rd instars (48 hour topical mortality)

| Mixture | | Mortality Tests | | | | | |
|---|---|---|---|---|---|---|---|
| Methomyl μg/insect | Potentiator μg/insect | A X/15 | B X/30 | C X/30 | D X/30 | E X/30 | Total | Kill % |
| 1.7 | 1.7 | | 12 | | | | 12/30 | 40 |
| 2.5 | 2.5 | 4 | | 7 | 20 | 11 | 42/105 | 40 |
| 3.5 | 3.5 | | 17 | | | | 17/30 | 57 |
| 5. | 5. | 3 | | 17 | 17 | 15 | 52/105 | 50 |
| 7. | 7. | | 22 | | | | 22/30 | 73 |
| 10. | 10. | 10 | | 23 | 26 | 19 | 78/105 | 74 |
| 14. | 14. | | 27 | | | | 27/30 | 90 |
| 20. | 20. | | | 24 | 30 | 24 | 78/90 | 87 |
| 28. | 28. | 28 | | | | | 28/30 | 93 |
| Control | | 0 | 0 | 0 | 0 | 0 | 0/135 | 0 |

$LD_{50} = 3.6$  $SR_{50} = 27.$
$LD_{95} = 43.$  $SR_{95} = 190.$ 1,1,1-trifluoro-N-(3-phenylpropyl)methanesulfonamide alone gives no mortality at 28 μg/insect.

TABLE 1F

Methomyl plus N—[(2-(4-chlorophenyl)ethyl]-1,1,1-trifluoromethanesulfonamide (potentiator) (1:1 weight ratio) against methomyl-resistant *Heliothis virescens* 3rd instars (48 hour topical mortality).

| Mixture | | Mortality Tests | | | |
|---|---|---|---|---|---|
| Methomyl μg/insect | Potentiator μg/insect | A X/15 | B X/30 | C X/30 | D X/30 |
| 2.5 | 2.5 | 5 | 11 | 15 | 16 |
| 5. | 5. | 6 | 20 | 23 | 13 |
| 10. | 10. | 8 | 24 | 25 | 19 |
| 20. | 20. | | 30 | 28 | 20 |
| Control | | 0 | 0 | 0 | 0 |

| Mixture | | | | | | | |
|---|---|---|---|---|---|---|---|
| Methomyl μg/insect | Potentiator μg/insect | E X/30 | F X/30 | G X/30 | H X/30 | Total | Kill % |
| 2.5 | 2.5 | 19 | 14 | 12 | 20 | 112/225 | 50 |
| 5. | 5. | 20 | 22 | 16 | 24 | 144/225 | 64 |
| 10. | 10. | 23 | 20 | 25 | 27 | 171/225 | 76 |
| 20. | 20. | 29 | 25 | 25 | 30 | 187/210 | 89 |
| Control | | 0 | 0 | 0 | 0 | 0/225 | 0 |

$LD_{50} = 2.6$  $SR_{50} = 37.$
$LD_{95} = 46.$  $SR_{95} = 180.$

N-[(2-(4-chlorophenyl)ethyl)]-1,1,1-trifluoromethanesulfonamide alone gives no mortality at 20 μg/insect.

TABLE 1G

Methomyl plus 1,1,1-trifluoro-N—[(2-(4-methoxyphenyl)-ethyl)]methanesulfonamide (potentiator) (1:1 weight ratio) against methomyl-resistant *Heliothis virescens* 3rd instars (48 hour topical mortality).

| Mixture | | Mortality Tests | | |
|---|---|---|---|---|
| Methomyl μg/insect | Potentiator μg/insect | A X/15 | Total | Kill % |
| 2.5 | 2.5 | 2 | 2/15 | 13 |
| 5. | 5. | 4 | 4/15 | 27 |
| 10. | 10. | 6 | 6/15 | 40 |
| Control | | 0 | 0/15 | 0 |
| $LD_{50} = 15.$ | | | $SR_{50} = 6.4$ | |
| $LD_{95} = 220.$ | | | $SR_{95} = 38.$ | |

1,1,1-trifluoro-N-[(2-(4-methoxyphenyl)ethyl)]methanesulfonamide alone gives no mortality at 10 μg/insect.

TABLE 1H

Methomyl plus 1,1,1-trifluoro-N—(6-phenylhexyl)methanesulfonamide (potentiator) (1:1 weight ratio) against methomyl-resistant *Heliothis virescens* larvae (48 hour topical mortality).

| Mixture | | Mortality Tests | | | |
|---|---|---|---|---|---|
| Methomyl μg/insect | Potentiator μg/insect | A X/30 | B X/30 | Total | Kill % |
| 2.5 | 2.5 | 17 | 16 | 33/60 | 55 |
| 5. | 5. | 20 | 17 | 37/60 | 62 |
| 10. | 10. | 28 | 25 | 53/60 | 88 |
| 20. | 20. | 25 | 24 | 49/60 | 82 |
| Control | | 0 | 0 | 0/60 | 0 |
| $LD_{50} = 1.9$ | | | | $SR_{50} = 51.$ | |
| $LD_{95} = 64.$ | | | | $SR_{95} = 130.$ | |

1,1,1-trifluoro-N-(6-phenylhexyl)methanesulfonamide alone gives no mortality at 20 μg/insect.

TABLE 1I

Methomyl plus N—(1,3-benzodioxol-5-ylmethyl)-1,1,1-trifluoromethanesulfonamide (potentiator) (1:1 weight ratio) against methomyl-resistant *Heliothis virescens* 3rd instars (48 hour topical mortality).

| Mixture | | Mortality Tests | | |
|---|---|---|---|---|
| Methomyl μg/insect | Potentiator μg/insect | A X/30 | Total | Kill % |
| 2.5 | 2.5 | 10 | 10/30 | 33 |
| 5. | 5. | 14 | 14/30 | 47 |
| 10. | 10. | 19 | 19/30 | 63 |
| Control | | 0 | 0/30 | 0 |
| $LD_{50} = 5.6$ | | | $SR_{50} = 17.$ | |
| $LD_{95} = 110.$ | | | $SR_{95} = 75.$ | |

N-(1,3-benzodioxol-5-ylmethyl)-1,1,1-trifluoromethanesulfonamide alone gives no mortality at 10 μg/insect.

EXAMPLE 2

Potentiation of Carbofuran by Trifluoromethanesulfonamides

Mixtures of carbofuran and sulfonamide synergists (1:1 weight ratio) and carbofuran alone were dissolved in various amounts of acetone, providing solutions of various strengths. A single dose of each mixture was applied topically to carbamate-susceptible *Heliothis virescens*, 3rd instars. For each test one microliter of solution mixture was applied to the prothorax of the insects. After treatment, the insects were allowed to remain in isolation chambers (1 oz. cup, filled to 25% capacity with Bioserv ® synthetic diet) for 48 hours, after which time the insects were scored for mortality. The results of the carbofuran alone and carbofuran plus potentiator were compared. Since the sulfonamides were found to have only a very minor effect by themselves at the concentrations tested, their concentrations were ignored for purposes of calculating the value of the kill ratio, K, where $$K = \frac{\text{Percentage of insects killed by mixture}}{\text{Percentage of insects killed by carbofuran alone}}$$

All the mixtures reported below, applied against carbamate-susceptible *Heliothis virescens*, 3rd instars, generated K values of greater than unity, indicating synergistic effect.

TABLE 2

| Mixture | | Mortality Tests | | | | |
|---|---|---|---|---|---|---|
| Carbofuran μg/insect | Potentiator μg/insect | A X/10 | B X/30 | Total | Kill % | Kill ratio |
| Carbofuran alone | | | | | | |
| 0.61 | | | 0 | 0/30 | 0 | |
| 1.2 | | | 2 | 2/30 | 7 | |
| 2.5 | | | 3 | 3/30 | 10 | |
| 5. | | | 3 | 3/30 | 10 | |
| 10. | | 0 | 5 | 5/40 | 13 | |
| 20. | | | 4 | 4/30 | 13 | |
| Carbofuran plus N—[(2-(4-bromophenyl)ethyl)]-1,1,1-trifluoromethanesulfonamide | | | | | | |
| 0.61 | 0.61 | | 4 | 4/30 | 13 | ND* |
| 1.2 | 1.2 | | 3 | 3/30 | 10 | 1.4 |
| 2.5 | 2.5 | | 4 | 4/30 | 13 | 1.3 |
| 5. | 5. | | 4 | 4/30 | 13 | 1.3 |
| 10. | 10. | | 11 | 11/30 | 37 | 2.8 |
| 20. | 20. | | 11 | 11/30 | 37 | 2.8 |
| Carbofuran plus 1,1,1-trifluoro-N—(3-phenylpropyl)-methanesulfonamide | | | | | | |
| 0.61 | 0.61 | | 4 | 4/30 | 13 | ND* |
| 1.2 | 1.2 | | 4 | 4/30 | 13 | 1.9 |
| 2.5 | 2.5 | | 7 | 7/30 | 23 | 2.3 |
| 5. | 5. | | 7 | 7/30 | 23 | 2.3 |
| 10. | 10. | 6 | 12 | 18/40 | 45 | 3.5 |
| 20. | 20. | | 8 | 8/30 | 27 | 2.1 |
| Carbofuran plus N—(1,3-benzodioxol-5-ylmethyl)-1,1,1-trifluoromethanesulfonamide | | | | | | |
| 10. | 10. | 6 | | 6/10 | 60 | 4.6 |

ND* = not detectable, denominator = 0.

EXAMPLE 3

Potentiation of Carbaryl by Trifluoromethanesulfonamides

Mixtures of carbaryl and N-(3-phenylpropyl)-1,1,1-trifluoromethanesulfonamide (1:2 weight ratio), carbaryl alone and N-(3-phenylpropyl)-1,1,1-trifluoromethanesulfonamide alone were dissolved in a solvent mixture of Duponol ®/water/acetone (volume ratio: 1/3000/3000). Various doses of each mixture were sprayed onto 40 susceptible *Heliothis virescens*, 3rd instar larvae. The spray apparatus was set up to deliver 10 ml of solution at 30 p.s.i. from a height of seven inches as the insects were conveyed under an atomizing nozzle at 33 ft/min. The insects were sprayed and held for 48 hours in 8 oz. plastic cups with enough Bioserv ® synthetic diet to cover the bottom of the cups. After 48 hours, the insects were scored for mortality. The data were analyzed to calculate the $LD_5$, $LD_{50}$, an $LD_{95}$ (dosage which kills 5, 50, and 95% respectively, of the treated insects) by a Bliss-Finney log dosage-probit analysis. Since N-(3-phenylpropyl)-1.1,1-trifluoromethanesulfonamide was found to give no mortality at the highest concentration tested, its concentrations were ignored for the purposes of analyzing the data and calculating the SR values.

N-(3-phenylpropyl-1,1,1-trifluoromethanesulfonamide potentiated carbaryl on susceptible *Heliothis virescens*, 3rd instars, as indicated by SR values which are greater than unity.

TABLE 3

| Mixture | | | Mortality Tests | | | |
|---|---|---|---|---|---|---|
| Concentration (%) of Carbaryl in the Solution | Concentration (%) of Potentiator in the Solution | A X/40 | Total | Kill % | | |
| Carbaryl alone | | | | | | |
| 0.005 | | 5 | 5/40 | 13 | LD$_5$ | 0.023 |
| 0.0125 | | 1 | 1/40 | 3 | | |
| 0.025 | | 3 | 3/40 | 8 | LD$_{50}$ | 1.2 |
| 0.05 | | 3 | 3/40 | 8 | | |
| 0.125 | | 8 | 8/40 | 20 | LD$_{95}$ | 62. |
| 0.25 | | 17 | 17/40 | 43 | | |
| 0.5 | | 19 | 19/40 | 48 | | |
| 5. | 27 | 27/40 | 68 | | | |
| Control | | 3 | 3/40 | 8 | | |
| Carbaryl plus 1,1,1-trifluoro-N—(3-phenylpropyl)-methanesulfonamide | | | | | | |
| 0.005 | 0.01 | 2 | 2/40 | 5 | LD$_5$ | 0.0078 |
| 0.0125 | 0.025 | 1 | 1/40 | 3 | SR$_5$ | 2.9 |
| 0.025 | 0.05 | 12 | 12/40 | 30 | LD$_{50}$ | 0.28 |
| 0.05 | 0.1 | 11 | 11/40 | 28 | SR$_{50}$ | 4.3 |
| 0.125 | 0.25 | 16 | 16/40 | 40 | LD$_{95}$ | 10. |
| 0.25 | 0.5 | 16 | 16/40 | 40 | SR$_{95}$ | 6.2 |
| 0.5 | 1. | 27 | 27/40 | 68 | | |
| Control | | 3 | 3/40 | 8 | | |

EXAMPLE 4

Potentiation of Thiodicarb by Trifluoromethanesulfonamides

Mixtures of thiodicarb and trifluoromethanesulfonamide (1:10 weight ratio), and thiodicarb alone, and trifluoromethanesulfonamide alone were dissolved in a solvent mixture of Duponol ®/water/acetone (volume ratio: 1:3000:3000). Various dosages of each mixture were sprayed on carbamate-resistant *Heliothis virescens*, 3rd instar larvae. The spray apparatus was set up to deliver 10 ml of solution at 30 p.s.i. from a height of seven inches as the insects passed under the nozzle at 33 ft/min. After being sprayed, the insects were held for 48 hours in 8 oz. cups with enough Bioserv ® synthetic diet to cover the bottom of the cups. After 48 hours, the insects were scored for mortality. The data were analyzed to calculate the LD$_{50}$ by a Bliss-Finney log dosage-probit analysis. Since the sulfonamides were found to have only a very small observable effect at the highest concentration tested, their concentrations were ignored for the purpose of calculating the LD$_{50}$.

All the tested sulfonamides potentiated thiodicarb, as indicated by synergism ratio (SR) values greater than unity.

TABLE 4A

Thiodicarb alone against carbamate-resistant *Heliothis virescens* 3rd instars (48 hour spray mortality).

| Concentration (%) of Thiodicarb in Solution | Mortality Tests | | | | |
|---|---|---|---|---|---|
| | A X/40 | B X/40 | C X/40 | Total | Kill % |
| 0.0025 | 4 | 3 | 5 | 12/120 | 10 |
| 0.005 | 8 | 13 | 5 | 26/120 | 22 |
| 0.01 | 0 | 7 | 7 | 14/120 | 12 |
| 0.025 | 9 | 9 | 6 | 24/120 | 20 |
| 0.05 | 16 | 9 | 5 | 30/120 | 25 |
| 0.1 | 10 | 4 | 15 | 29/120 | 24 |
| Control | 5 | 1 | 1 | 7/120 | 6 |
| LD$_{50}$ = 12 | | | | | |

TABLE 4B

Thiodicarb plus N—[(2-(4-bromophenyl)ethyl)]-1,1,1-trifluoromethanesulfonamide (potentiator) (1:10 weight ratio) against carbamate-resistant *Heliothis virescens* 3rd instars (48 hour spray mortality).

| Mixture | | Mortality Tests | | | |
|---|---|---|---|---|---|
| Concentration (%) of Thiodicarb in Solution | Concentration (%) of Potentiator in Solution | A X/40 | B X/40 | Total | Kill % |
| 0.0025 | 0.025 | 10 | 5 | 15/80 | 19 |
| 0.005 | 0.05 | 5 | 5 | 10/80 | 13 |
| 0.01 | 0.1 | 11 | 12 | 23/80 | 29 |
| 0.025 | 0.25 | 14 | 18 | 32/80 | 40 |
| 0.05 | 0.5 | 14 | 18 | 32/80 | 40 |
| 0.1 | 1. | 24 | 28 | 52/80 | 65 |
| | 1. | 6 | 8 | 14/80 | 18 |
| Control | | 5 | 1 | 6/80 | 8 |
| LD$_{50}$ = 0.070 | | | SR$_{50}$ = 170. | | |

TABLE 4C

Thiodicarb plus 1,1,1-trifluoro-N—(3-phenylpropyl)-methanesulfonamide (potentiator) (1:10 weight ratio) against carbamate-resistant *Heliothis virescens* 3rd instars (48 hour spray mortality).

| Mixture | | Mortality Tests | | |
|---|---|---|---|---|
| Concentration (%) of Thiodicarb in Solution | Concentration (%) of Potentiator in Solution | A X/40 | Total | Kill % |
| 0.0025 | 0.025 | 4 | 4/40 | 10 |
| 0.005 | 0.05 | 4 | 4/40 | 10 |
| 0.01 | 0.1 | 5 | 5/40 | 13 |
| 0.025 | 0.25 | 15 | 15/40 | 38 |
| 0.05 | 0.5 | 14 | 14/40 | 35 |
| 0.1 | 1. | 27 | 27/40 | 68 |
| | 1. | 5 | 5/40 | 13 |
| Control | | 1 | 1/40 | 4 |
| LD$_{50}$ = 0.066 | | SR$_{50}$ = 180. | | |

TABLE 4D

Thiodicarb plus N—[(2-(4-chlorophenyl)ethyl)]-1,1,1-trifluoromethanesulfonamide (potentiator) (1:10 weight ratio) against carbamate-resistant *Heliothis virescens* 3rd instars (48 hour spray mortality).

| Mixture | | Mortality Tests | | |
|---|---|---|---|---|
| Concentration (%) of Thiodicarb in Solution | Concentration (%) of Potentiator in Solution | A X/40 | Total | Kill % |
| 0.0025 | 0.025 | 4 | 4/40 | 10 |

TABLE 4D-continued

Thiodicarb plus N—[(2-(4-chlorophenyl)ethyl)]-1,1,1-trifluoromethanesulfonamide (potentiator) (1:10 weight ratio) against carbamate-resistant *Heliothis virescens* 3rd instars (48 hour spray mortality).

| Mixture | | | | |
|---|---|---|---|---|
| Concentration (%) of Thiodicarb in Solution | Concentration (%) of Potentiator in Solution | A X/40 | Total | Kill % |
| 0.005 | 0.05 | 11 | 11/40 | 28 |
| 0.01 | 0.1 | 10 | 10/40 | 25 |
| 0.025 | 0.25 | 10 | 10/40 | 25 |
| 0.05 | 0.5 | 16 | 16/40 | 40 |
| 0.1 | 1. | 19 | 19/40 | 48 |
|  | 1. | 6 | 6/40 | 15 |
| Control |  | 1 | 1/40 | 3 |
| $LD_{50} = 0.17$ |  | $SR_{50} = 71.$ | | |

EXAMPLE 5

Methomyl Plus Trifluoromethanesulfonamide Against Susceptible *Heliothis virescens*

Methomyl plus sulfonamide and methomyl alone were mixed into a solvent mixture of Duponol®/water/acetone (volume ratio: 1/3000/3000). The weight ratio of methomyl to sulfonamide varied from 1:1 to 1:10. The susceptible *Heliothis virescens* 3rd instars were sprayed at 30 p.s.i. nozzle pressure from a height of 7 inches as they were conveyed under the nozzle at 33 ft/min. After being sprayed, the insects were held for 48 hours in 8 oz. plastic cups with enough Bioserv® synthetic diet to cover the bottom of the cup. At the end of 48 hours, the insects were scored for mortality. The $LD_{50}$ and $LD_{95}$ were calculated by the Bliss-Finney method and the synergism ratios for the respective LD values were calculated.

TABLE 5A

Methomyl alone against susceptible *Heliothis virescens* 3rd instars (48 hour spray mortality).

| Concentration (%) of Methomyl in Solution | Mortality Tests | | | |
|---|---|---|---|---|
| | A X/40 | B X/40 | Total | Kill % |
| 0.001 | 4 | 9 | 13/80 | 16 |
| 0.0025 | 9 | 9 | 18/80 | 23 |
| 0.005 | 9 | 15 | 24/80 | 30 |
| 0.01 | 22 | 24 | 46/80 | 58 |
| 0.025 | 25 | 25 | 50/80 | 63 |
| 0.05 | 33 | 35 | 68/80 | 85 |
| Control | 2 | 0 | 2/80 | 3 |
| $LD_{50} = 0.010$ | | | | |
| $LD_{95} = 0.22$ | | | | |

TABLE 5B

Methomyl plus N—[(2-(4-chlorophenyl)ethyl)]-1,1,1-trifluoromethanesulfonamide (potentiator) (1:10 weight ratio) against susceptible *Heliothis virescens* 3rd instars (48 hour spray mortality).

| Mixture | | | | |
|---|---|---|---|---|
| Concentration (%) of Methomyl in Solution | Concentration (%) of Potentiator in Solution | A X/40 | Total | Kill % |
| 0.001 | 0.01 | 4 | 4/40 | 10 |
| 0.0025 | 0.025 | 14 | 14/40 | 35 |
| 0.005 | 0.05 | 21 | 21/40 | 53 |
| 0.01 | 0.1 | 29 | 29/40 | 73 |
| 0.025 | 0.25 | 35 | 35/40 | 88 |

TABLE 5B-continued

Methomyl plus N—[(2-(4-chlorophenyl)ethyl)]-1,1,1-trifluoromethanesulfonamide (potentiator) (1:10 weight ratio) against susceptible *Heliothis virescens* 3rd instars (48 hour spray mortality).

| Mixture | | | | |
|---|---|---|---|---|
| Concentration (%) of Methomyl in Solution | Concentration (%) of Potentiator in Solution | A X/40 | Total | Kill % |
| 0.05 | 0.5 | 39 | 39/40 | 98 |
|  | 1. | 10 | 10/40 | 25 |
| Control |  | 0 | 0/40 | 0 |
| $LD_{50} = 0.0047$ |  | $SR_{50} = 2.1$ | | |
| $LD_{95} = 0.040$ |  | $SR_{95} = 5.5$ | | |

TABLE 5C

Methomyl plus 1,1,1-trifluoro-N—(3-phenylpropyl)-methanesulfonamide (potentiator) (1:10 weight ratio) against susceptible *Heliothis virescens* 3rd instars (48 hour spray mortality).

| Mixture | | | | |
|---|---|---|---|---|
| Concentration (%) of Methomyl in Solution | Concentration (%) of Potentiator in Solution | A X/40 | Total | Kill % |
| 0.001 | 0.01 | 8 | 8/40 | 20 |
| 0.0025 | 0.025 | 10 | 10/40 | 25 |
| 0.005 | 0.05 | 15 | 15/40 | 38 |
| 0.01 | 0.1 | 19 | 19/40 | 48 |
| 0.025 | 0.25 | 35 | 35/40 | 88 |
| 0.05 | 0.5 | 37 | 37/40 | 93 |
|  | 1. | 0 | 0/40 | 0 |
| Control |  | 0 | 0/40 | 0 |
| $LD_{50} = 0.0066$ |  | $SR_{50} = 1.5$ | | |
| $LD_{50} = 0.093$ |  | $SR_{95} = 2.4$ | | |

TABLE 5D

Methomyl plus 1,1,1-trifluoro-N—(3-phenylpropyl)-methanesulfonamide (potentiator) (1:1 weight ratio) against susceptible *Heliothis virescens* 3rd instars (48 hour spray mortality).

| Mixture | | | | |
|---|---|---|---|---|
| Concentration (%) of Methomyl in Solution | Concentration (%) of Potentiator in Solution | A X/40 | Total | Kill % |
| 0.001 | 0.001 | 1 | 1/40 | 3 |
| 0.0025 | 0.0025 | 7 | 7/40 | 18 |
| 0.005 | 0.005 | 16 | 16/40 | 40 |
| 0.01 | 0.01 | 17 | 17/40 | 43 |
| 0.025 | 0.025 | 28 | 28/40 | 70 |
| 0.05 | 0.05 | 36 | 36/40 | 90 |
|  | .1 | 1 | 1/40 | 3 |
| Control |  | 2 | 2/40 | 5 |
| $LD_{50} = 0.011$ |  | $SR_{50} = 0.91$ | | |
| $LD_{50} = 0.1$ |  | $SR_{95} = 2.2$ | | |

TABLE 5E

Methomyl plus N—[(2-(4-bromophenyl)ethyl)]-1,1,1-trifluoromethanesulfonamide (potentiator) (1:10 weight ratio) against susceptible *Heliothis virescens* 3rd instars (48 hour spray mortality).

Mortality Tests

| Mixture Concentration (%) of Methomyl in Solution | Concentration (%) of Potentiator in Solution | A X/40 | Total | Kill % |
|---|---|---|---|---|
| 0.001 | 0.01 | 11 | 11/40 | 28 |
| 0.0025 | 0.025 | 10 | 10/40 | 25 |
| 0.005 | 0.05 | 20 | 20/40 | 50 |
| 0.01 | 0.1 | 26 | 26/40 | 65 |
| 0.025 | 0.25 | 34 | 34/40 | 85 |
| 0.05 | 0.5 | 37 | 37/40 | 93 |
| | 1.0 | 10 | 10/40 | 25 |
| Control | | 0 | 0/40 | 0 |
| $LD_{50} = 0.0047$ | | $SR_{50} = 2.1$ | | |
| $LD_{95} = 0.086$ | | $SR_{95} = 2.6$ | | |

What is claimed is:

1. An insecticidal or miticidal composition of:
   (1) methomyl; and
   (2) 1,1,1-trifluoro-N-(3-phenylpropyl)-methanesulfonamide as potentiator for methomyl; where the weight ratio of potentiator to methomyl is form about 1:1 to 10:1.

2. A method for the control of insects or mites comprising applying to a locus to be protected an insecticidally or miticidally effective amount of a composition of claim 1.

* * * * *